United States Patent [19]

Kampf

[11] Patent Number: 4,589,540
[45] Date of Patent: May 20, 1986

[54] SAMPLE CONTAINER TRANSFER MECHANISM

[75] Inventor: Richard S. Kampf, Costa Mesa, Calif.

[73] Assignee: Beckman Instruments, Inc., Fullerton, Calif.

[21] Appl. No.: 660,562

[22] Filed: Oct. 15, 1984

Related U.S. Application Data

[63] Continuation of Ser. No. 328,342, Dec. 7, 1981, abandoned.

[51] Int. Cl.⁴ .............................................. B65G 47/00
[52] U.S. Cl. ...................................... 198/345; 250/328
[58] Field of Search ............... 198/339, 341, 345, 472, 198/580, 795; 250/328; 141/130

[56] References Cited

U.S. PATENT DOCUMENTS

| | | | |
|---|---|---|---|
| 3,163,756 | 12/1964 | Meeder et al. | 250/71.5 |
| 3,270,202 | 8/1966 | Long et al. | 250/71.5 |
| 3,859,528 | 1/1975 | Luitwieler, Jr. et al. | 250/328 |
| 3,890,505 | 6/1975 | Olson | 250/328 |
| 3,905,453 | 9/1975 | Frank | 187/17 |
| 3,919,554 | 11/1975 | Frank | 187/17 |
| 4,122,936 | 10/1978 | Johnson | 198/339 |
| 4,147,250 | 4/1979 | Schulz | 198/472 |
| 4,242,582 | 12/1980 | Kampf | 250/328 |
| 4,244,458 | 1/1981 | Kampf | 198/339 |

*Primary Examiner*—Joseph E. Valenza
*Assistant Examiner*—Daniel R. Alexander
*Attorney, Agent, or Firm*—W. H. May; P. R. Harder; S. R. Markl

[57] ABSTRACT

A transfer mechanism for movement of sample containing vials from a first position to a second position in an analyzer instrument such as a liquid scintillation or a gamma counting device. The apparatus is particularly adaptable where available space is limited. A flexible transport member permits the transformation of movement in one direction into movement in another direction. Sensors and adjusting screws are incorporated into the apparatus for precisely controlling the travel distance of the transport member as well as precisely orienting the direction of the transport member.

8 Claims, 7 Drawing Figures

SAMPLE CONTAINER TRANSFER MECHANISM

BACKGROUND OF THE INVENTION

This is a continuation of application Ser. No. 328,342, filed Dec. 7, 1981 now abandoned.

This invention relates generally to transfer mechanisms and, more particularly, to the movement of sample containing vials within some type of analytical instrument.

One particular application of the present invention is in a liquid scintillation instrument as well-known in a gamma counter instrument. With respect to liquid scintillation, its techniques have been widely adapted to measure the count rate or activity of samples containing radionuclides. The radioactive sample typically a beta emitter is placed in direct contact with a liquid scintillation medium by dissolving or suspending the sample within the medium. The liquid scintillation medium comprises a solvent or solvents, typically toluene or dioxane, and solute or solutes present in a few percent by weight of the solution. The liquid scintillation solution consisting of the solvent(s), the solute(s), and the radioactive sample is placed within a sample vial for measuring the radioactive emissions within the liquid scintillator. It is theorized that most of the kinetic energy from the nuclear decay events of the radioactive sample is absorbed by the solvent and then transferred to the solute which emits photons as visible light flashes or scintillations. The amount of emitted light is proportional to the amount of energy absorbed from the decay events. The scintillations are detected by a photomultiplier tube or other light responsive device which converts the energy of each scintillation to a voltage pulse having a pulse height proportional to the energy of the detected scintillation.

Part of the mechanics of operating a liquid scintillation instrument is the necessity to transfer the sample containing vial having the radioactive sample from the carrier mechanism on which a series of vials are located into a detector chamber wherein the counting operation occurs as set forth above. Because the radioactive counting is very sensitive, it is accomplished in a sealed detector chamber. Any external background light or background radiation would affect the counting by the highly sensitive photomultiplier. Typically, only a very small passageway is used for entry of the vial into the detector chamber. Consequently, it is important that some type of transfer mechanism be available to accurately and precisely transport the sample containing vial from the platform area of the instrument into the detector chamber through a passageway which provides the entry into the detector chamber.

In smaller tabletop models of liquid scintillation instruments or gamma counter instruments it is important that the transfer mechanism be compact. Attention is directed to prior art U.S. Pat. Nos. 3,919,554 and 4,122,936 which disclose transfer mechanisms for use in a liquid scintillation instrument. The transfer mechanism in the '554 patent is constructed of a flat tape member that moves within a flat sheath wherein some horizontal travel is translated into vertical travel. Movement of the flat member is generated by a reel. Because of the flat configuration of the tape member, adjustment of the direction of travel is limited. In the '936 arrangement, a coil spring is moved by a pulley to translate horizontal movement into vertical movement. The coil spring travels in a guide tube prior to entry into the counting chamber. The presence of the guide tube inhibits the utilization of a light seal which can shut onto the transfer mechanism and seal the counting chamber.

It is also important with respect to the utilization of a transfer mechanism in a liquid scintillator that it operate in cooperation with some type of valving mechanism that is used to seal the detector chamber against the entry of light from external sources or the escape of light from the scintillations while the sample containing vial is in the counting chamber. Otherwise, the entry of external light or the escape of light could prevent accurate counting of scintillations. For this reason, compatibility with the detector chamber is an important feature which must be addressed when designing a transfer mechanism for movement of a sample vial into a detector chamber in a liquid scintillator. The prior arrangements discussed above do not properly address this concern.

Another problem in some prior art transfer mechanisms is the stability of the sample containing vial as it is being transported in a vertical direction for movement into the detector chamber. The vial must be laterally supported during its vertical movement. Otherwise, the vial may become displaced or not be properly oriented to permit its entry into the detection chamber.

SUMMARY OF THE INVENTION

The present invention is directed to an elongate flexible transport member wherein longitudinal movement of the transport member in one direction is translated into another direction and wherein an unsupported end of the transport member is guided in a straight line path between a first position and a second position. The elongated flexible transport member contacts the container or vial for movement. An adjustment mechanism is provided to accurately align an elongated transport member so that its movement into and out of the passageway to the detector chamber is in accurate alignment. The invention includes a mechanism which automatically corrects any jamming which may occur in the operation of the elongated transport member.

The present transfer mechanism incorporates a conveniently replaceable transfer or contact end on the transport member in the event the contact end should become contaminated.

The compact design of the present invention allows for its utilization in conjunction with adjacent similarly designed transfer mechanisms in a single instrument such as a gamma counter wherein more than one transfer mechanism is necessary. The overall configuration of the transfer mechanism allows for the placement of multiple sensors to control the precise movement necessary for the function being performed.

The stability of the vial is addressed in the present invention. A stabilizing member contacts a portion of the sample carrying vial as it moves vertically from its first position to its second position. This stabilizing member holds the sample carrying vial in the correct position on the transport member as it moves vertically into and out of the detector chamber.

The transport member is designed to be compatible with a light seal to completely seal the detector chamber from any exterior environment. Attention is directed to copending patent application entitled Light Seal for Liquid Scintillation Instrument Ser. No. 328,341, filed on Dec. 7, 1981 in the names of Richard S.

Kampf and Henry G. Dowling and assigned to the assignee of the present invention.

DETAILED DESCRIPTION OF THE DRAWINGS

DETAILED DESCRIPTION OF THE INVENTION

For exemplary purposes, the transfer mechanism of the present invention will be discussed with respect to its use in a liquid scintillation device. In such an arrangement, a plurality of sample containing vials are positioned in a rack located on a transfer platform and moveable in a horizontal plane below a detection chamber. The transfer mechanism moves each vial in succession from a first position in the rack vertically to a second position in the chamber for scintillation counting and back to the first position. In moving the vials into the detection chamber, the transfer mechanism interfaces with a light blocking or light sealing device in order to seal the chamber while the scintillation counting is occurring.

Figure 6:
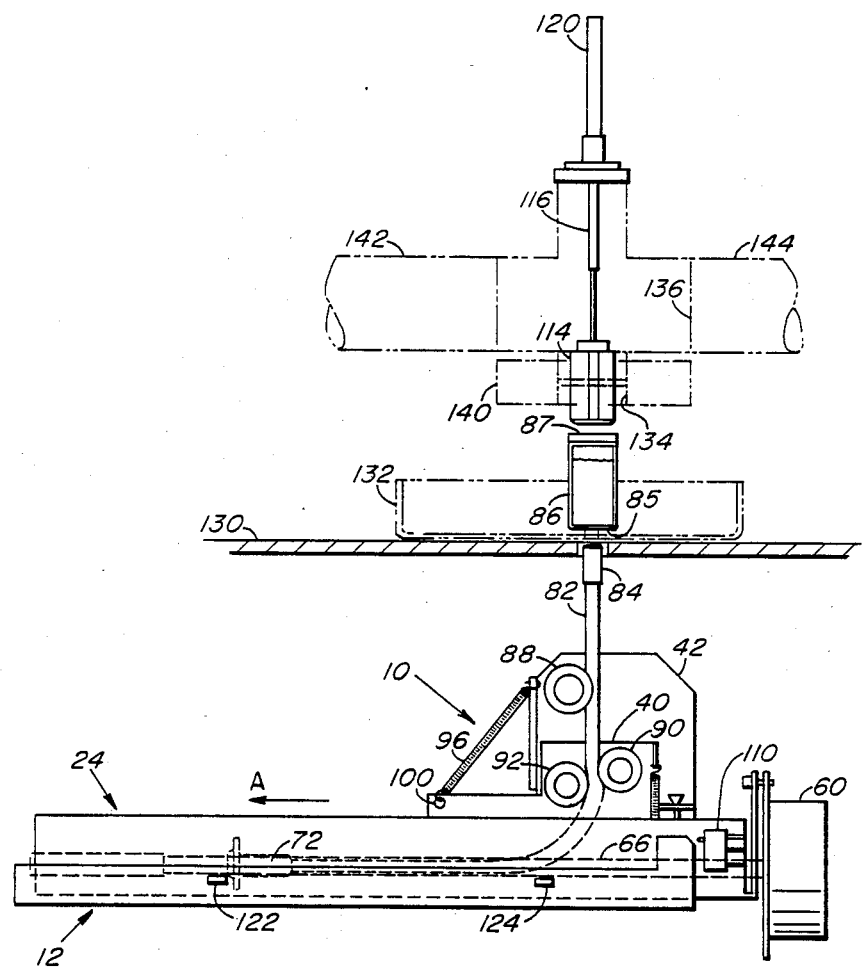
FIG. 6 is a schematic side elevation view of the present invention with the sample containing vial in the first position.
Figure 7:
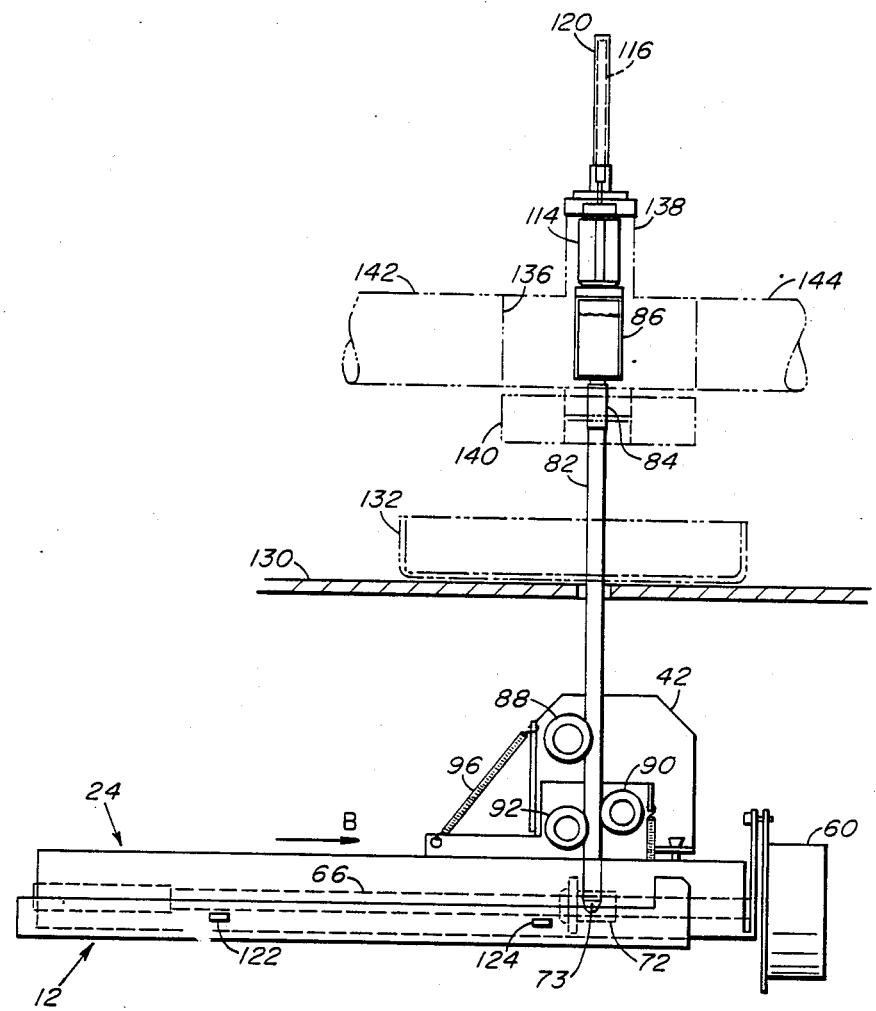
FIG. 7 is a somewhat schematic side elevational view similar to FIG. 6 of the sample carrying vial positioned within the detector chamber of a liquid scintillation instrument.

FIGS. 6 and 7 show a schematic arrangement of the relationship between the transfer mechanism 10 of the present invention with a liquid scintillation instrument. Briefly, in the operation of a liquid scintillation instrument, a rack 132 containing a plurality of sample-carrying vials 86 is positioned on a transfer platform 130. The rack 132 is indexed in a controlled manner so that each vial 86 is successively placed into alignment with a transport member or lifting spring 82 which contacts the bottom 85 of the vial to move it from its position on the platform 130 to a position within a detector chamber 136.

In the operation of the transfer mechanism the lifting spring 82 is moved by horizontal movement of a travel member 72 which is threadably engaged with an elongated screw 66. Operation of the motor 60 causes the travel member 72 to move toward and away from the motor 60. This movement causes a comparable movement by the contact end 84 of the lifting spring 82. As shown in FIG. 7, movement of the travel member 72 toward th motor 60 causes the contact end 84 of the lifting spring 82 to move the vial 86 into the detection chamber 136. A light valve 140 is closed on the contact end 84 of the travel member to seal the chamber 136. After the scintillation counting has been completed within the chamber 136, the light seal 140 is opened and the lifting spring 82 moves downward as the travel member 72 moves back to its position as shown in FIG. 6. As a result, the vial 86 is again in the rack 132. The transfer platform 130 indexes the rack to the next position so that the next vial is plced over the lifting spring 82 and the sequence is repeated.

Figure 1:
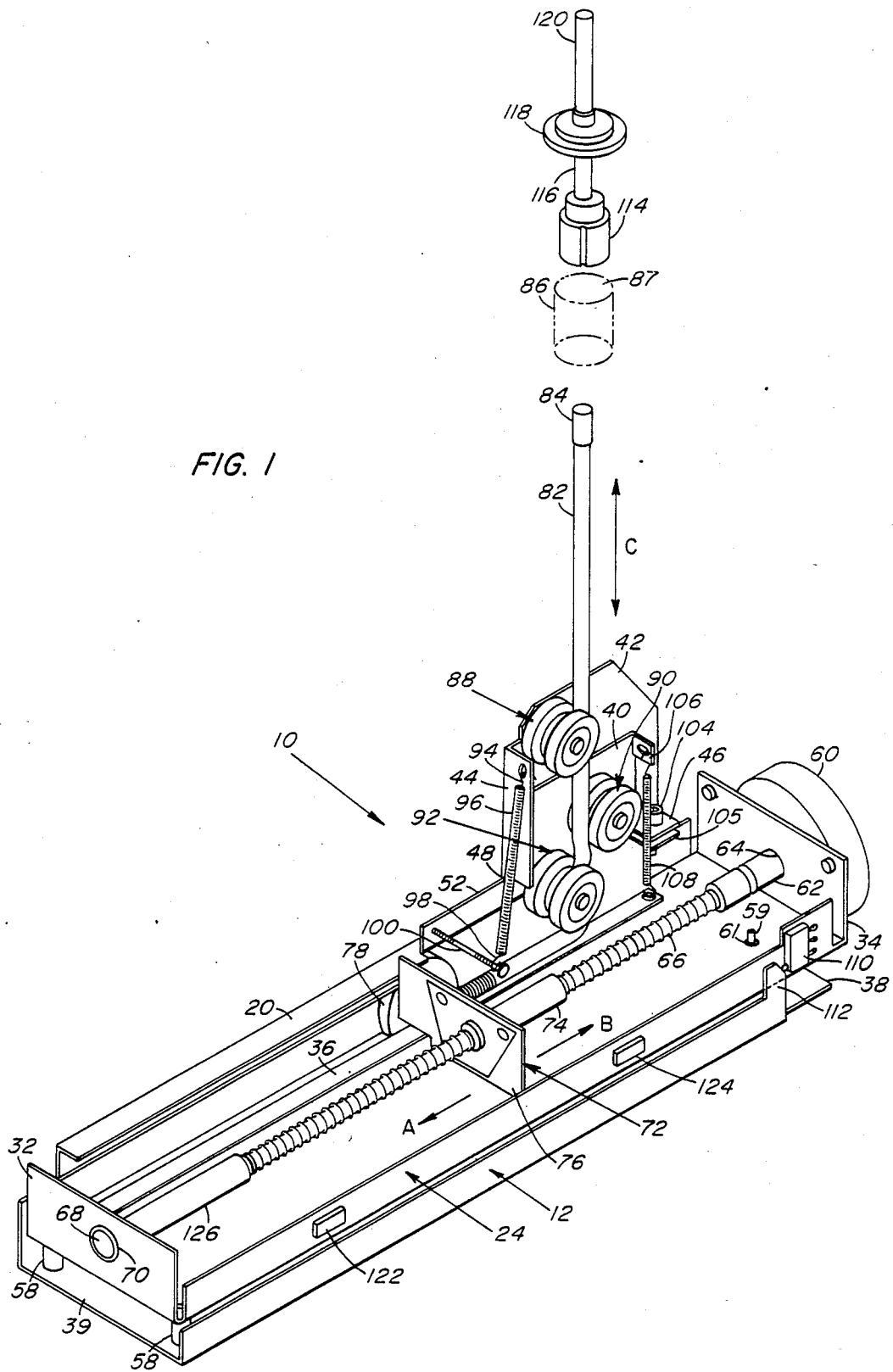
FIG. 1 is a perspective view of the transfer mechanism of the present invention.
Figure 2:
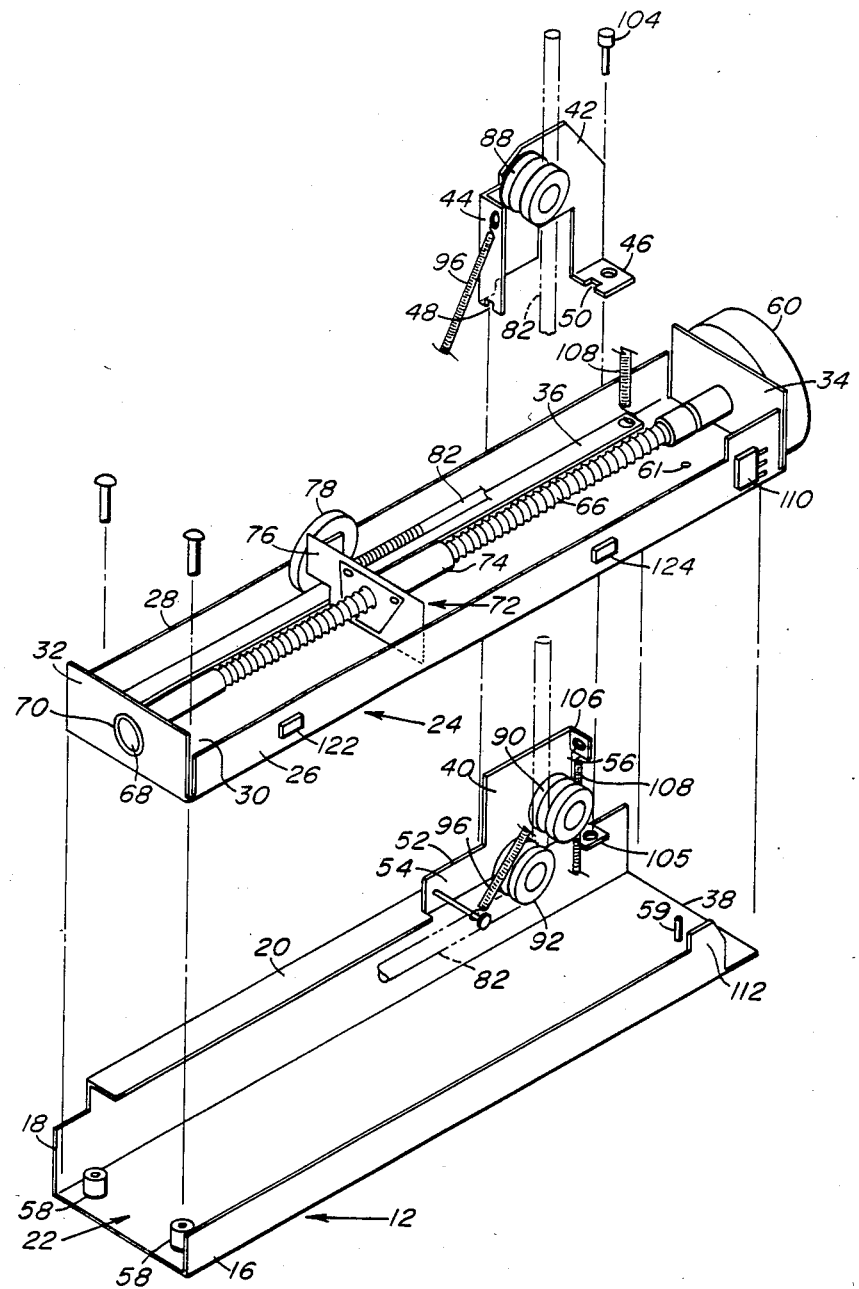
FIG. 2 is a perspective exploded view of the support base for the transfer mechanism.

The transfer or elevator mechanism 10 of the present invention in FIG. 1 has a base support member 12 which is secured by means not shown to the frame of the instrument in which it operates. As shown more clearly in FIG. 2, the base support member 12 is a single member having a general channel-like cross-sectional configuration with a horizontal bottom portion 14 bounded on its longitudinal edges by respective vertical longitudinal flanges 16 and 18. One vertical flange 16 is relatively short and has a uniform configuration, the other vertical flange 18 is higher and has an overhanging ledge portion 20. The interior area 22 formed by the bottom portion 14 and the vertical flanges 16 and 18 is designed to receive a carriage tray 24 which is dimensionally designed to fit between the vertical flanges 16 and 18 on the base support member 12. The carriage tray has two longitudinal vertical flanges 26 and 28 which extend upward from the bottom 30. A holder flange 32 is located at one end of the tray 24 while at the other end is a motor mount flange 34. Located in a slightly elevated position from the bottom 30 of the tray 24 is a longitudinal guide path 36.

Adjacent the motor end 38 of the base support 12 is a support wall 40 that is integrally formed and projected from the overhanging ledge 20. Designed for engagement with the support wall 40 is an adjustment frame 42 having a vertical pivot flange 44 and a horizontal pivot flange 46. Located in the vertical pivot flange 44 is a pivot notch 48 while similar pivot notch 50 is located in the horizontal pivot flange 46. The adjustment frame 42 is designed to rest in side-by-side generally parallel relationship with the support wall 40 of the base member 12. The pivot notch 48 is designed to pivotally rest on the upper edge 52 of a lower portion 54 of the support wall 40. A second horizontal pivot notch 50 in the adjustment frame is designed to engage the vertical edge 56 of the support wall 40.

As shown in FIG. 1, the carriage tray 24 is designed to have its holder end 32 pivotally attached by fastening means (not shown) through spacers 58 to the holder end 39 of the base support 12. The opposite end of the carriage tray adjacent the motor flange 34 is not secured in a fixed manner to the support base 12. However, a guide pin 59 is mounted on the support base 12 and slidably resides in aperture 61 in the opposite end of the carriage tray 24.

Attached to the motor support flange 34 is a reversible a.c. motor 60 which has a drive shaft connector 62 extending through the aperture 64 in the motor holding flange 34. Secured to the shaft connector 62 is an elongated threaded lead screw 66 which extends from the motor holder flange 34 the entire length of the carriage tray 24 to the holder flange 32. The opposite end 68 of the lead screw 66 is rotatably received in a self aligning bearing 70 mounted in the holder flange 32 of the carrier tray 24. Consequently, by activation of the reversible motor 60, it is possible for the lead screw to turn in either a clockwise direction or a counterclockwise direction.

Figure 3:
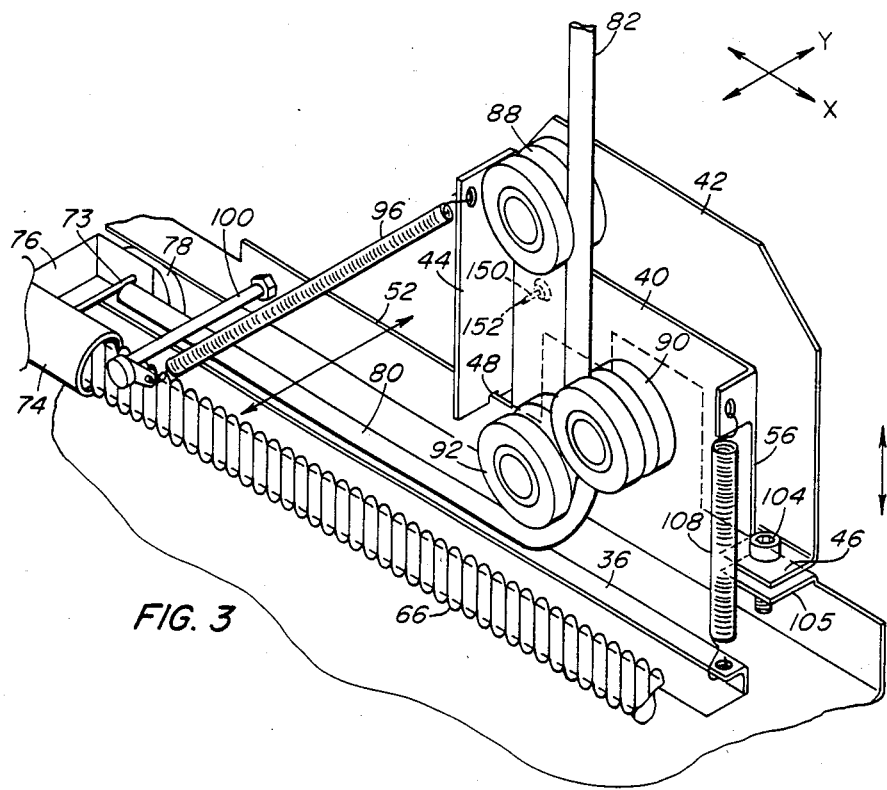
FIG. 3 is a perspective view of a portion of the transfer mechanism showing the adjustable feature for the transport members.

Threadably mounted on the lead screw 66 is a travel member 72 having a sleeve portion 74 and a flange member 76. The travel member 72 will move in either the direction of arrow A or the direction of arrow B, depending upon the direction of rotation caused by the motor 60. Connected to the flange 76 is a guide wheel 78 which rides in the carriage tray 24 under the ledge 20 of the base support member 12. Mounted between the guide wheel 78 and the sleeve portion 74 of the travel member 72 is a pivotal support bar 73 to which one end 80 of a transport member or lifting spring 82 is attached as shown in FIG. 3. The guide wheel 78 and the travel member 72 share in the support of the movement of the one end 80 of the lifting spring. The guide wheel 78 also acts as a retainer to keep the travel member 72 from rotating.

The lifting spring or transport member 82 is designed to provide the actual movement of a sample carrying vial 86 from its location in a rack to a location within a detector chamber in a liquid scintillation instrument. The lifting spring 82 is an elongated pretensioned coil spring which is designed to provide flexibility while maintaining inherent strength as necessary. Because the end 80 of the lifting spring 82 is connected to the pivotal support bar 73, the one end 80 of the lifting spring can pivot to a vertical direction when the travel member 72 is located below the roller set 92. This occurs when the lifting spring 82 is oriented at a complete extended position wherein the vial is positioned in the detection chamber as shown in FIG. 7.

The other end of the lifting spring 82 has a removable soft rubber tip which cooperates with a light seal adjacent the detector chamber as is explained in the previously mentioned copending patent application entitled Light Seal for a Liquid Scintillation Device. The removable tip 84 allows for convenient replacement if the tip should become contaminated. The lifting spring 82 is designed to ride on the guide path 36 formed in the bottom of the carriage tray 24. The guide path 36 provides support to the lifting spring 82 when it is in its horizontal position within the carriage tray 24. It should be noted that the lifting spring is not positioned in any type of a sheath, because the spring is designed with enough pretension and strength to withstand potential buckling during normal use.

The horizontal movement of the lifting spring is generated by the travel member 72 moving along the lead screw 66 is transposed into vertical movement. The lifting spring 82 must move a sample containing vial 86 from a position in a rack on the platform of the instrument upward a particular specified distance into a detector chamber. In order to accomplish the transposition of the lifting spring from a generally horizontal motion within the carriage tray 24 to a vertical orientation for movement in the direction of the arrow C in FIG. 1, a plurality of rollers 88, 90 and 92 are used. The rollers 90 and 92 are attached to the support wall 40 of the support base 12 while the roller 88 is attached to the adjusting frame 42. Each of the rollers 88, 90, and 92 are comprised of two side-by-side rollers in order to establish a groove in which the lifting spring 82 can travel on each of the rollers. Although the rollers 90 and 92 are of primary necessity for accomplishing the redirection of the lifting spring 82, it has been found that the additional or guide roller 88 is beneficial in order to provide for the desired adjustability in the direction of the lifting spring as will be explained in more detail. It should be noted that the roller 88 will impart a reverse bend on the lifting spring 82 after it leaves the roller 90. This is important for the positive control of the rollers 88, 90, and 92 on the directional movement of the lifting spring 82.

The use of the guide roller 88 has been determined to also be necessary as a guide to ensure that the flexible lifting spring 82 will track or move in a straight line as it moves vertically between the transfer platform 130 and the detection chamber 136 in FIG. 6. The bending caused by the main rollers 90 and 92 imparts a deflection in the lifting spring. This deflection causes the lifting spring to track in a nonstraight line as it moves vertically. The guide roller 88 acts as a guide to stabilize the lifting spring and compensate for the deflection caused by the two rollers 90 and 92 so that the lifting spring will track or move in a straight line travel path. This is very important because the lifting spring is not supported laterally in its vertical travel between the transfer platform and the detection chamber.

Attached to the vertical pivot flange 44 of the adjustment frame 42 in FIG. 1 is one end 94 of a biasing spring 96 which has its other end 98 connected to a positioning bolt 100. The free end 102 of the positioning bolt 100 orients the spring 96 at an approximate 45° angle with respect to the plane of the support wall 40 as well as an approximate 45° angle with respect to the plane of the vertical pivot flange 44. The horizontal pivot flange 46 on the adjustment frame 42 receives a threaded adjustment screw 104 which is also threaded in the anchoring flange 105 on the support base 12. The notch 50 in the horizontal flange 46 in FIG. 2 operates in conjunction with the pivot notch 48 in vertical flange 44 to accommodate the movement of the adjustment frame 42. The spring 96 places a loading on both of the notches 48 and 50.

Because the pivot notch 48 rests on the ledge 52 of the support wall 40, the biasing spring 96 tends to pull the adjustment frame 42 in such a manner that it wants to rotate in a counterclockwise direction about the pivot notch 48 with respect to FIG. 1. However, the threaded adjustment screw 104 which is connected to the support base maintains the amount of pivoting allowed of the adjustment frame 42.

The biasing spring 96 also tends to pull the adjustment frame 42 in a direction toward the support wall 40. An adjustment screw (not shown) is threaded into the adjustment frame 42 and contacts the back surface with respect to FIG. 1 of the support wall 40 to adjust the distance between the adjustment frame 42 and the support wall 40. These two types of adjustments with respect to the adjustment frame 42 will be explained in more detail with respect to the present invention's features of being able to adjustably orient the direction of the lifting spring 82 for its vertical movement.

Attached to an apertured flange 106 on the support wall in FIG. 1 is a holding spring 108 which is connected to the carriage tray 24. The holding spring 108 will maintain the motor end 34 of the carriage tray in a spaced relationship from the motor end 38 of the support base 12. If the lifting spring 82 would be blocked or jammed in its upward movement, continued movement of the travel member 72 would cause the lifting spring to force the motor end 34 of the tray to move down toward the motor end 38 of the support base 12. However, a switch 110 located on the motor end of the carriage tray would engage a tripping flange 112 on the motor end of the support base 12, causing the motor to reverse the movement of the travel member 72 and retract the spring to alleviate eliminate any jam. More detail with respect to this operation will be explained.

When the contact end or tip 84 of the lifting spring 82 contacts the bottom of the vial 86 in FIG. 1 and moves it in an upward direction away from the lifting mechanism 10, the vial must be maintained in a stable manner. Located directly above the vial 86 before it is lifted, is a weighted stabilizer member 114 which is connected to a telescoping rod 116. The telescoping rod 116 is connected to a fastening cap 118 which is attached above the detector chamber of the liquid scintillation device. A retracting tube 120 receives the telescoping rod 116 as it collapses during upward movement of the vial 86. Once the vial 86 is lifted from its carrying rack, its top 87 contacts the weighted member 114 which provides stability to the vial as it moves upward. This will ensure that the vial does not become askewed or misaligned with respect to its movement through the passageway into the detector chamber.

To control the travel distance of the travel member 72 which in turn controls the travel of the lifting spring 82, a pair of sensors 122 and 124 are located on the vertical side flange 26 of the carriage tray 24. When the travel member 72 is adjacent the retract sensor 122, it will generate a signal for the motor 60 to stop, because the lifting spring has been retracted far enough to allow the vial carrying rack to index to another position. When the lifting spring has been extended the correct distance to place the vial properly within the detector chamber, the travel member 72 will be adjacent the advance sensor 124 which will generate a signal for the motor 60 to stop. It should be noted that a limit sleeve 126 is surmounted on the lead screw 66 adjacent the holder end 32 of the carriage tray. The limit sleeve 126 will also restrict movement of the travel member if necessary.

Attention is now directed to FIGS. 6 and 7 relating to the overall operation of the present device. The elevator or transfer mechanism 10 is located in some position in a liquid scintillation instrument below the carrier platform 130 on which travel the tube or vial racks 132 containing a plurality of sample containing vials 86. Once the rack has been indexed to its correct position so that the vial 86 is directly over the contact end 84 of the retracted lifting spring or transport member 82, the motor 60 is activated to rotate the lead screw 66 and move the travel member 72 in the direction of arrow B. As a result of the horizontal movement of the travel member 72, the portion of the lifting spring adjacent the travel member will also travel horizontally on the guide path until it reaches the area of the sets of rollers 88, 90 and 92 wherein it will be turned to a vertical direction for upward movement. The horizontal movement of the travel member 72 results in vertical movement of the contact end 84 of the lifting spring 82. Consequently, the contact member 84 will engage the bottom 85 of the vial 86. The vial will then be moved upward, wherein it will engage the weighted member 114 which is located approximately a quarter of an inch above the top 87 of the vial. The lifting spring 82 will continue to travel several inches upward through the light valve passage 134 that is located just below the detection chamber 136. As the weighted member 114 is moved upward, its telescoping rod 116 will collapse within the retraction tube 120.

As shown in FIG. 7, the advance sensor 124 is oriented on the carriage tray in such a position that, when the travel member contacts it, the vial 86 will be in its correct orientation within the detector chamber 136 and the lifting spring will stop movement. Further, the weighted member 114 will be housed completely within its housing 138. Once the vial 86 is in its proper orientation within the detector housing, the light valve mechanism 140 will operate to enclose the light valve around the soft rubber tip 84 of the lifting spring to prevent the entry of any exterior environment to the chamber. The photomultipliers 142 and 144 will then operate in conjunction with the sample containing the radionuclides. Once the counting has been completed with respect to the sample in the vial 86 and the light seal is opened, the motor 60 is activated to operate in the reverse direction to move the travel member 72 in the direction of arrow A in FIG. 7, causing the contact end 84 of the lifting spring to move downward, carrying the vial 86 as well as the weghted member 114 for stability. The vial is then received back into its rack 132 and the contact member end 84 of the lifting spring 82 is retracked below the platform 130. The rack 132 is indexed to the next position to place the next vial over the lifting spring 82 and the sequence is repeated. It should be noted that the proper position of the contact end 84 under the platform 130 is determined by having the travel member 72 contact the retract switch 122 which will generate a signal to turn off the motor 60. Also as a safety feature, the limit sleeve 126 is surmounted on the lead screw 66 in order to limit any further movement of the travel member 72.

In some instances it may be necessary over a period of continued use of the device to provide adjustment in the direction in which the free end or contact end 84 of the lifting spring moves to avoid some type of misalignment in the movement of the vial in the liquid scintillation device. The present invention, as shown in FIG. 3, incorporates the unique ability to precisely adjust the direction of the contact end 84 so that it will be always in proper alignment for contact and movement of the vial. The adjustment frame 42 has a vertical flange 44 pivotally connected by its pivot notch 48 to the edge 52 of the support wall 40. The horizontal pivot flange 46 of the frame 42 is adjustably connected by the adjustment screw 104 to the anchoring flange 105 of the support wall 40. The biasing spring 96 tends to cause the adjustment frame 42 to pivot about the pivotal notch 48 in a counterclockwise direction. However, the adjustment screw 104 limits the amount of pivoting in the counterclockwise direction of the adjustment frame 42 by the spring 96. By loosening or tightening the adjustment screw 104, the lifting spring 82 can be adjusted in the X axis in FIG. 3

It should be noted also that the biasing spring 96 tends to force the adjustment frame 42 toward the support wall 40. Again, the adjustment frame 42 is pivoting on the edge 52 in the pivot notch 48. Shown in phantom is a restriction screw 150 that is threaded into the adjustment frame 42 and has its end 152 contact the back surface of the support wall 40. Therefore, movement of the support frame 42 toward the support wall 40 is limited by the adjustment of the screw 150. By turning the adjustment screw 150 in one direction or another direction, the lifting spring 82 is adjusted in the Y axis. Therefore, the combined adjustment of the screws 104 and 150 allow for the desired adjustment in either or both the Y and X axes. This is accomplished by the fact that the guide roller set 88 holding and guiding the lifting spring is connected to the adjustment frame 42

Figure 4:
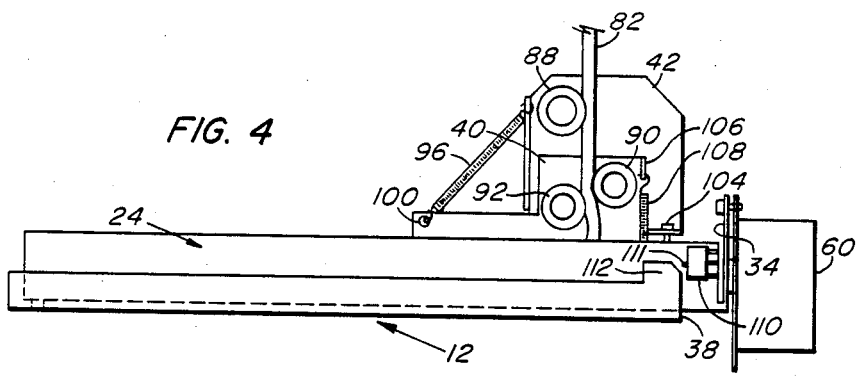
FIG. 4 is a side elevational view of the present invention during normal operation.
Figure 5:
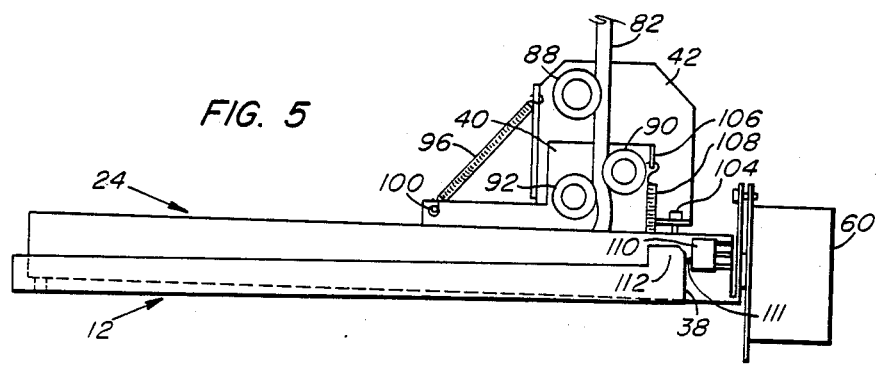
FIG. 5 is a side elevational view showing the operation of the anti-jamming feature of the present invention.

Although the present invention is designed to avoid any blocking or jamming of the lifting sring 82, an added feature of means for automatically correcting any jamming of the lifting spring is incorporated into the present invention. The operation of this added feature is based on the automatic reversing of the operation of the motor to retract the lifting spring. Attention is directed to FIGS. 4 and 5 wherein the holding spring 108 is shown connected to the support wall 40 and connected to the motor end 34 of the carriage tray 24. Attached adjacent the motor end 34 of the tray is the switch 110 having a contact lever 111. Formed on the motor end 38 of the support base 12 is a contact flange 112. Any impediment to the upward movement of the lifting spring 82 as the travel member moves toward the motor 60 results in a reactive force downward against the biasing of the holding spring 108. The motor end 34 of the carrier tray 24 moves downward toward the support base 12 where the contact lever 111 engages the ledge 112 on the support base. A signal is generated to reverse the operation of the motor 60 and retract the lifting spring 82. Once the lifting spring is retracted, the holding spring 108 will again raise the motor end 34 of the carriage tray 24 out of engagement with the contact ledge 112 on the support base 12.

The adjustment feature, as described above with respect to FIG. 3, as well as the anti-jamming feature described above with respect to FIGS. 4 and 5 in conjunction with the elongated lifting spring configuration, provides a unique elevator system for use in an instrument such as a liquid scintillation device. Not only can the lifting mechanism be accurately adjusted for the correct orientation for the direction of its movement, but also it can be automatically unjammed if such a circumstance would occur. Also it should be noted that the use of the third or guide roller 88 permits the use of a laterally unsupported elongate lifting spring which will track or move in a straight line for moving the vial vertically.

Although the present lifting or transfer mechanism has been discussed with respect to its application to a liqud scintillation device, the principles set forth with respect to this device are applicable for the transfer of any type of small container from a first position to a second position. Further, although the above description is directed to the lifting of the sample vial from a platform vertically upward into a detection chamber, the system is equally applicable for moving a sample vial from a platform downward into an analyzer chamber. It is envisioned that the basic concept of the present invention is applicable for use in providing horizontal movement of a sample containing vial or some other type of container. All of the features of the present invention would appear to be equally applicable regardless of the particular direction of movement.

What is claimed is:

1. A transfer assembly for moving a container between a first position and a second position, said assembly comprising:
   a support base;
   an elongated flexible transport member postioned on said support base and having one end contacting said container;
   means for moving said one end of said transport member between said first and second positions;
   means mounted on said support base for directing travel of said transport member from a first longitudinal direction to a second longitudinal direction at an anglee to said first longitudinal direction;
   means mounted adjacent said directing means for guiding said one end of said transport member in a straight line travel path unsupported between said first and second positions, said guiding means comprising an adjustment frame pivotally connected to said support base;
   first means for biasing said frame in one direction;
   second means for biasing said frame in a second lateral direction;
   means for supporting said transport member mounted to said frame;
   means provided with said frame for adjusting the amount of pivotal movement of said frame relative to said support base caused by said first biasing means; and
   means provided with said frame for adjusting the amount of pivotal movement of said frame relative to said support base caused by said second biasing means.

2. The transfer assembly of claim 1 additionally comprising
   container stabilizing means positioned above said container; and
   means for movably mounting said stabilizing means in close proximity to said container when said container is in said first position, said stabilizing means contacting said container when said container moves from said first position to provide support to said container as it moves between said first and second psitions.

3. A transfer assembly for moving a container between a first position and a second position, said assembly comprising:
   a support base;
   an elongated flexible transport member positioned on said support base and having one end contacting said container;
   means for moving said one end of said transport member between said first and second positions comprising an elongate actuator member mounted on said support base and having threads along substantially its entire length and a threaded member engaging the threads and riding on said actuator member and connected to said transport member to drive said transport member as the actuator member is operated;
   means mounted on said support base for directing travel of said transport member from a first longitudinal direction to a second longitudinal direction at an angle to said first longitudinal direction;
   means mounted adjacent said directing means for guiding said one end of said transport member in a straight line travel path unsupported between said first and second positions.

4. The transfer assembly of claim 3 additionally comprising means for automatically reversing said moving means when said one end of said transport member engages an obstruction between said first and second positions.

5. A container transfer apparatus for moving a container along a vertical path comprising:
   base support means;
   an elongate flexible transport member having inherent strength to resist flex and straighten, one end of said transport member adapted to engage and move said container;
   means for reciprocally moving said transport member in a longitudinal direction by applying alternating compressive and tensile forces to the opposing end of said transport member;
   bending means mounted to said base means for directing said transport member from movement in a generally horizontal direction to movement in a generally vertical direction comprising a pair of cooperating guide rollers spaced in opposing position with a horizontal offset so that a first roller receives said transport member within a groove concentrically formed around said first roller and provides a curved surface around which said transport member may bend by lateral force applied to said member by the second guide roller also comprising a groove to provide lateral support for said member, said guide rollers providing bilateral support through rolling control of said transport member within their respective grooves to substantially redirect longitudinal movement of said transport member; and a stabilizing means positioned above said bending means to receive said transport means for adjustably guiding said transport member in unsupported movement along a vertical path to contact said container comprising a third grooved guide roller positioned with a horizontal offset in opposing relation to said second roler of said bending means to receive said transport member within the groove of said third roller to provide adjustable lateral support to direct said transport member in vertical movement, said third guide roller slightly bending said transport member over the surface of said second guide roller in a direction opposing the bending of said transport member over said first guide roller.

6. A transfer assembly as defined in claim 4, wherein said reversing means comprises:

a carriage tray having one end connected to said support base, said carriage tray holding said transport member, said support base being stationary;

means connected to the other end of said carriage tray for biasing said tray away from said support base; and means on one of said tray and said support base for sensing the movement of said tray toward said base when said transport member is blocked from moving completely from said first position to said second position, said sensing means generating a signal to said moving means to reverse the direction of movement of said transport member.

7. A transfer assembly as defined in claim 6, wherein said biasing means comprises a spring having one end connected to said support base and the other end connected to said carriage tray.

8. A transfer assembly as defined in claim 6, wherein said sensing means comprises an electrical switch.

* * * * *